(12) United States Patent
Kausek

(10) Patent No.: US 7,520,852 B1
(45) Date of Patent: Apr. 21, 2009

(54) ERECTION STIMULATOR APPARATUS AND METHOD

(76) Inventor: Douglas W. Kausek, 2990 Wilson Rd. NE., Somerset, OH (US) 43783-9732

( * ) Notice: Subject to any disclaimer, the term of this patent is extended or adjusted under 35 U.S.C. 154(b) by 56 days.

(21) Appl. No.: 11/420,669

(22) Filed: May 26, 2006

(51) Int. Cl.
*A61F 5/00* (2006.01)
(52) U.S. Cl. ......................................... 600/38
(58) Field of Classification Search ............. 600/38–40; 128/845, 897
See application file for complete search history.

(56) References Cited

U.S. PATENT DOCUMENTS

| | | | | |
|---|---|---|---|---|
| 992,821 | A * | 5/1911 | Stewart | 174/135 |
| 3,446,206 | A | 5/1969 | De Lano | |
| 3,633,572 | A * | 1/1972 | Wiggins | 600/41 |
| 4,022,196 | A | 5/1977 | Clinton | |
| 4,262,662 | A | 4/1981 | Allinson | |
| 4,262,663 | A | 4/1981 | Allinson | |
| 4,362,152 | A | 12/1982 | Gorokhovsky et al. | |
| 4,429,689 | A | 2/1984 | Yanong | |
| 4,440,183 | A * | 4/1984 | Miller | 600/41 |
| 4,449,521 | A | 5/1984 | Panzer | |
| 4,455,717 | A * | 6/1984 | Gray | 24/115 R |
| 4,643,175 | A | 2/1987 | Chapman | |
| 4,653,484 | A | 3/1987 | Cannon | |
| 4,776,325 | A | 10/1988 | Etingher | |
| 4,785,802 | A * | 11/1988 | Blount | 600/39 |
| 4,872,447 | A | 10/1989 | Tsirjulnikov et al. | |
| 4,953,542 | A | 9/1990 | Tsirjulnikov et al. | |
| 5,065,744 | A | 11/1991 | Zusmanovsky | |
| 5,133,735 | A * | 7/1992 | Slater et al. | 606/205 |
| 5,171,314 | A * | 12/1992 | Dulebohn | 606/113 |
| 5,218,974 | A | 6/1993 | Garrett | |
| 5,517,729 | A * | 5/1996 | Shaffer | 24/30.5 R |
| 5,911,686 | A | 6/1999 | Kohut | |
| 6,416,460 | B1 | 7/2002 | Jochum | |
| 6,436,031 | B1 | 8/2002 | Salib | |
| 6,579,229 | B1 | 6/2003 | Nan | |
| 6,793,620 | B1 | 9/2004 | Droznin et al. | |
| 6,923,755 | B2 | 8/2005 | Norma | |
| 2005/0124853 | A1 | 6/2005 | Norma | |

* cited by examiner

*Primary Examiner*—Samuel G Gilbert
(74) *Attorney, Agent, or Firm*—Aileen Law; Sara A. Gossman; A Law Firm, P.C.

(57) ABSTRACT

The disclosed apparatus assists in developing, maintaining and enhancing the firmness of a user's erection. The apparatus is an erection stimulator that is comprised generally of a loop with a handle that is positionable between the user's legs. The handle further comprises at least one ridge that creates pressure in the perineum region proximate to said scrotum and rectum, i.e. the space along the sides and behind the scrotum and extending to the rectum. This pressure may help stimulate arousal while the apparatus may physically assist in retaining blood in the penis. The disclosed apparatus may further comprise at least one crest on the ridge(s) to further develop, maintain and enhance the firmness of a user's erection.

19 Claims, 2 Drawing Sheets

ERECTION STIMULATOR APPARATUS AND METHOD

FIELD OF ART

The disclosed apparatus and method relate to an erection stimulator which may assist in developing, maintaining and enhancing the firmness of a user's erection. More specifically, the erection stimulator comprises generally a loop or yoke, hereinafter loop, and a handle, harness or rod, hereinafter handle, that is positionable between the user's legs. The handle further comprises at least one ridge that may create pressure against the user's bulbospongiosus muscle in the perineum region proximate to the scrotum and rectum, i.e. the area of the perineum near the bulbospongiosus muscle located behind the scrotum and extending to the rectum.

BACKGROUND

Many men suffer from sexual impotency or what is commonly referred to or defined as erectile dysfunction (ED). The term erectile dysfunction covers a broad range of disorders, but usually refers to the inability to obtain an adequate erection for satisfactory sexual activity. ED is a very common problem which affects most men at least once during their lifetime. ED affects the lives of many middle-aged men and their partners to one degree or another. Although it appears that the incidence of impotence varies with age, for various physical and psychological reasons, some men are not able to attain and maintain penile erections, rendering satisfactory intercourse difficult or impossible. This impotency can limit, hinder, or even essentially prevent men from participating in sexual conduct. There have been great strides to treat sexual impotence in men. A number of devices have been invented to assist, maintain or substitute for penile erection. In some cases, surgical implanting of prosthetic devices has been utilized.

SUMMARY OF THE DISCLOSURE

The disclosed apparatus and method provide a non-surgical approach to the treatment of ED. The disclosed apparatus may assist in developing, maintaining and enhancing the firmness of a user's erection. The erection stimulator comprises generally a loop sized to fit around and contain a portion of the user's penis and scrotum and a handle that is positionable between the user's legs. In the disclosed embodiment, the handle may further comprise at least one ridge that may create pressure against the bulbospongiosus muscle in the perineum region proximate to the scrotum and rectum, i.e. the area of the perineum near the bulbospongiosus muscle located behind the scrotum and extending to the rectum. The disclosed apparatus may further comprise at least one crest on the ridge(s) to develop, maintain and enhance the firmess of a user's erection.

Before explaining the disclosed embodiments in detail, it is to be understood that the embodiments are not limited in application to the details of the particular arrangements shown, since other embodiments are possible. Also, the terminology used herein is for the purpose of description and not of limitation. The embodiments and features thereof are described and illustrated in conjunction with systems, tools and methods which are meant to exemplify and to illustrate, not be limiting in scope.

DETAILED DESCRIPTION OF THE DRAWINGS

Figure 1:
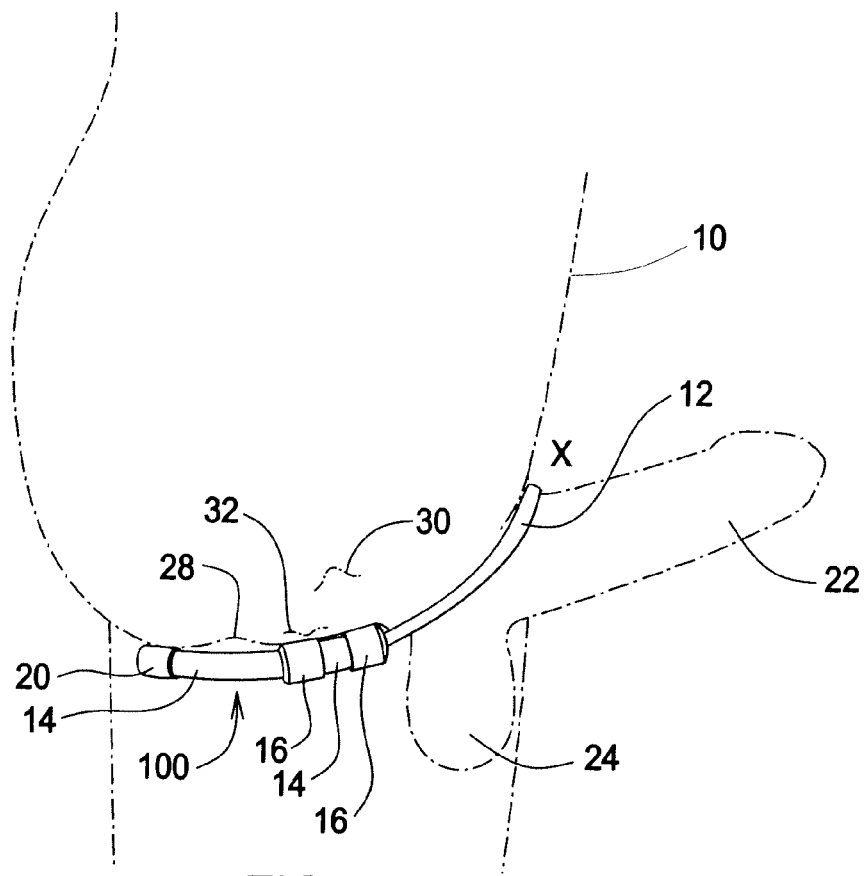
FIG. 1 is a side view of one embodiment of an erection stimulator in use.

FIG. 1 is a side view of one embodiment of an erection stimulator 100 applied to a user 10. In operation, loop 12 is placed around and contains a portion of the penis 22 and the scrotum 24. This may be best accomplished when penis 22 is in a flaccid or semi-flaccid state. While holding loop 12 at point X, above penis 22 and against the body of user 10, handle 14 is then positioned between the legs of user 10 and behind scrotum 24.

Figure 2:
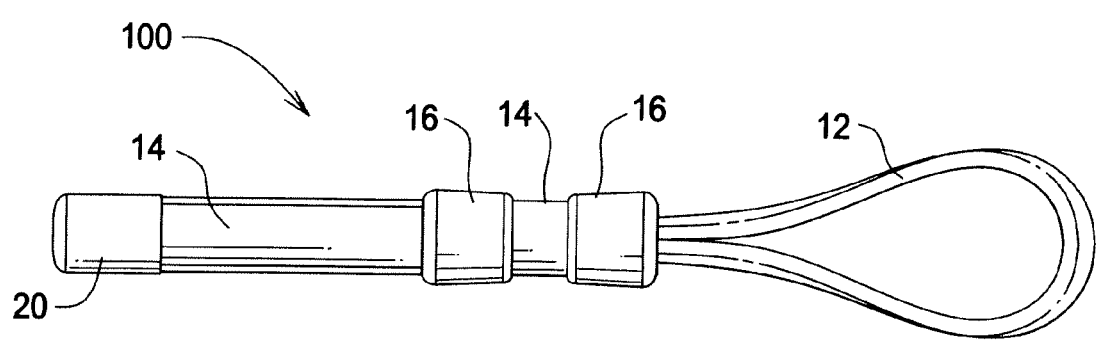
FIG. 2 is a top plan view of the erection stimulator of FIG. 1.

FIG. 2 is a top plan view of erection stimulator 100. As shown, erection stimulator 100 may include loop 12 and handle 14 with ridge(s) 16. Handle 14 may include optional cap 20 for the comfort of user 10.

Loop 12 may be made of 12/2 ground wire, however, the material of construction is offered only by way of example and not of limitation as other suitable materials that encompass and/or offer a method of constriction around penis 22 and scrotum 24 may be utilized. Furthermore, loop 12 may be of any size and shape although it is shown as arcuate. An end portion of loop 12 may be inserted into a handle 14 comprising any suitable material. For example, one embodiment of handle 14 envisions the use of about ⅝" to about ½" heater hose. However, other constructions are possible. For example, a non-hollow handle of any suitable diameter may be chosen. Optional cap 20 may also comprise any suitable material. One embodiment utilizes a rubberized ¾" end cap.

Ridge(s) 16 and/or crests 18 serve to stimulate perineum 32. As shown in FIGS. 1, 2, one embodiment of ridge(s) 16 utilizes rubberized, hollowed out ¾" end caps. The embodiments of FIGS. 3-8 display varying sizes, shapes and textures a ridge(s) 16 and crest 18 may have. Any number of ridges/crests could be implemented and/or interchanged on handle 14 if desired. Ridge(s) 16 and crests 18 are not limited by the embodiments shown.

Figure 3:
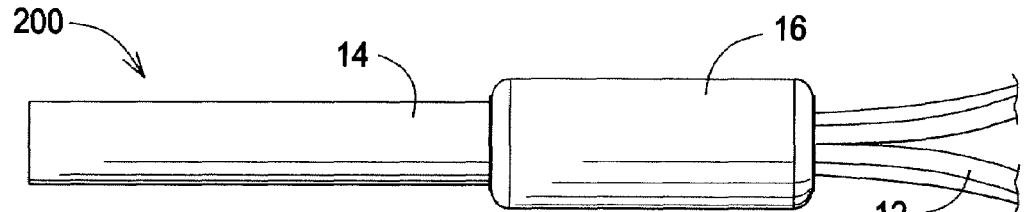
FIGS. 3-8 illustrate ridges and/or crests of varying size, shape and texture.
Figure 4:
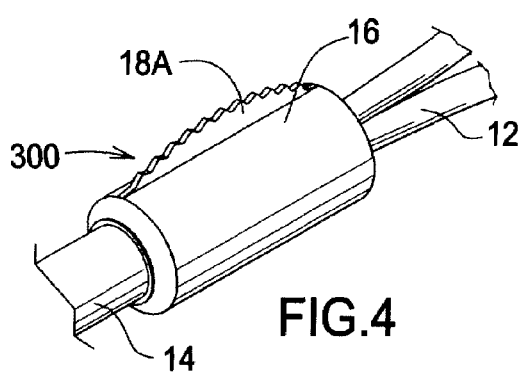
Figure 5:
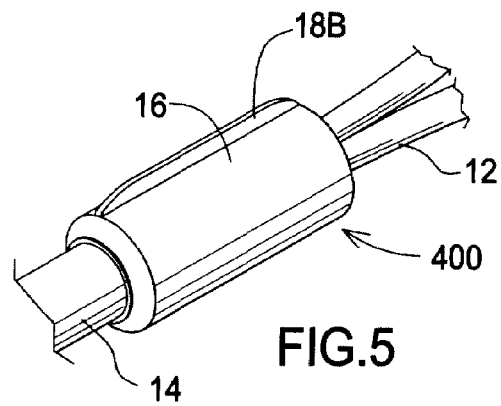
Figure 6:
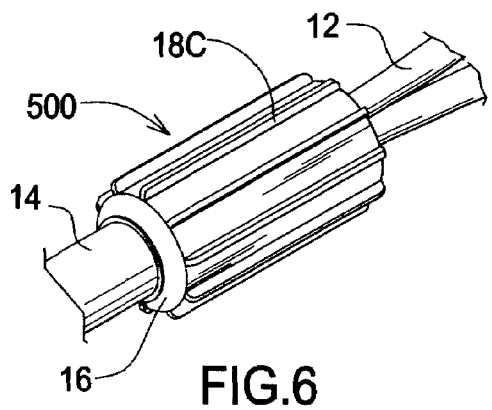
Figure 7:
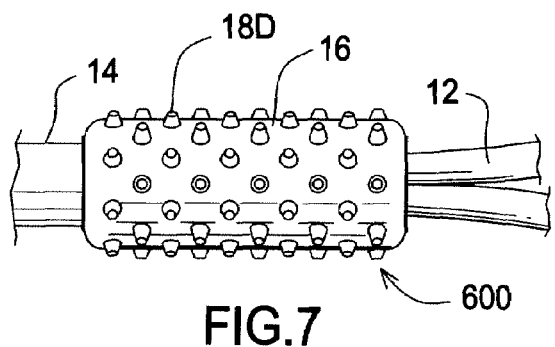
Figure 8:
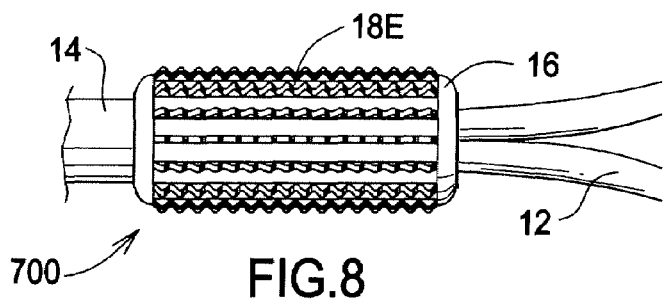

In the erection stimulator 200 of FIG. 3, a bottom portion of loop 12 is shown. An upper portion of handle 14 is covered by ridge 16. In this embodiment, perineum 32 may be stimulated by ridge 16 and/or handle 14. FIGS. 4-8 illustrate erection stimulators 300, 400, 500, 600 and 700. In all embodiments shown, an upper portion of handle 14 is partially covered by ridge 16. Depending on the preference of user 10, various stimuli can be incorporated. Crests 18 may be mounted to ridge(s) 16 to add points of stimulus. Crests 18A, 18B, 18C, 18D, 18E may be incorporated in erection stimulators 300, 400, 500, 600 and 700 to stimulate perineum 32. Crests 18A, 18B, 18C, 18D, 18E are presented by way of example and not of limitation. Any suitable ridge or crest size, shape and/or texture may be utilized and still fall within the scope of the disclosure. Erection stimulators 100, 200, 300, 400, 500, 600 and 700 generally operate in the same manner.

In some cases, user 10 may choose to reconfigure or adjust loop 12. For example, the user may remove loop 12 entirely from handle 14 of erection stimulator 100 before placing loop 12 around a portion of penis 22 and scrotum 24 at which time the ends of loop 12 may be reinserted into handle 14. A reassembled erection stimulator 100 may then be positioned between the legs of user 10 and behind scrotum 24.

In general, handle 14 may be adjusted against perineum 32. Perineum 32 is located below and along the sides of the bulbospongiosus muscle 30 extending between the scrotum 24 and the rectum 28. Thus, handle 14, ridge(s) 16 and/or crests 18 may rest against perineum 32. If desired, user 10 may shorten the circumference of loop 12 to further contain a portion of penis 22 and scrotum 24 outside of loop 12. Decreasing the diameter of loop 12 may help maintain the scrotum 24 on the outside of loop 12 which could position handle 14, ridge(s) 16 and/or crests 18 against user 10 for increased arousal.

User 10 may also adjust loop 12 by decreasing the diameter of loop 12 by sliding handle 14 and/or loop 12 towards each other which could create additional pressure against the bulbospongiosus muscle 30 to stimulate arousal. Decreasing the diameter of loop 12 may physically assist in retaining blood in penis 22.

Arousal may be further pronounced with the application of muscular pressure on handle 14 from the thighs (not shown) of user 10, causing consistent or sporadic pressure on perineum 32 as desired. Arousal may also be attained with the degree of curvature of handle 14 against perineum 32.

To remove erection stimulator 100, 200, 300, 400, 500, 600 or 700, user 10 may choose to allow penis 22 to return to a semi-flaccid state. The diameter of loop 12 may be increased to facilitate, if necessary, the removal of erection stimulator 100, 200, 300, 400, 500, 600 or 700 from penis 22 and scrotum 24.

While a number of exemplifying features and embodiments have been discussed above, those of skill in the art will recognize certain modifications, permutations, additions and subcombinations thereof. Other alternative embodiments of the present apparatus and method could be easily employed by those skilled in the art. No limitation with respect to the specific embodiments disclosed herein is intended or should be inferred. Each apparatus embodiment described herein has numerous equivalents.

I claim:

1. An apparatus for stimulating a penile erection, the apparatus comprising:
    a loop adapted to encircle a portion of a user's penis and scrotum;
    a rod housing a substantial portion of an end of said loop;
    said rod having a first ridge located along at least one longitudinal edge of said rod to stimulate a perineum region proximate to said user's scrotum and rectum; and
    wherein said loop is movable toward said rod to decrease the diameter of said loop, said decrease in diameter causing said first ridge to be positioned between said user's legs against said perineum region proximate to said scrotum and rectum, thereby enabling and sustaining stimulation of said region by at least said first ridge, said decrease in diameter further causing a constriction of said penis to occur to sustain a penile erection.

2. The apparatus of claim 1, wherein said first ridge further comprises at least one crest.

3. The apparatus of claim 2, wherein said at least one crest further comprises at least one uneven edge to enhance a stimulation of said perineum region.

4. The apparatus of claim 2, wherein said at least one crest further comprises at least one smooth edge.

5. The apparatus of claim 1 further comprising a second ridge slidable on said rod and positioned adjacent said first ridge, whereby a depression is formed therebetween, said second ridge capable of stimulating said perineum region.

6. An apparatus for stimulating a penile erection, the apparatus comprising:
    a length curved to form a loop, whereby the ends of said length are positioned adjacent from one another and said loop is adapted to encircle a portion of a user's penis and scrotum;
    wherein said ends are housed within a rod, thereby forming a handle positionable along a substantial portion of said user's perineum region;
    said handle slidable in a forward direction to decrease a diameter of said loop, said decrease in diameter causing said loop to enable and sustain a penile erection; and
    wherein said decrease in diameter further causes said first ridge to be positioned between said user's legs against said perineum region, whereby said first ridge stimulates said perineum region proximate to said scrotum and rectum.

7. The apparatus of claim 6, wherein said first ridge further comprises at least one crest.

8. The apparatus of claim 7, wherein said at least one crest further comprises at least one uneven edge to enhance a stimulation of said perineum region.

9. The apparatus of claim 7, wherein said at least one crest further comprises at least one smooth edge.

10. The apparatus of claim 6 further comprising a second ridge slidable on said handle and positioned adjacent said first ridge, whereby a depression is formed therebetween and capable of stimulating said perineum region.

11. An apparatus for stimulating a penile erection, the apparatus comprising:
    a handle housing a substantial portion of an end of a loop means, said loop means adapted for placement around a portion of a penis and scrotum, said loop means being adjustable to enable and sustain a penile erection;
    wherein said handle is positionable along a substantial portion of a user's perineum region;
    said handle having a ridge means located along a longitudinal edge of said handle, said handle slidable in a forward direction toward said loop; and
    said ridge means functioning to create a pressure point on a perineum region proximate to said scrotum and rectum to maintain said penile erection.

12. The apparatus of claim 11, wherein said ridge means further comprises at least one crest means to extend vertically beyond a longitudinal edge of said ridge means to further stimulate said perineum region.

13. The apparatus of claim 12, wherein said at least one crest means further comprises at least one uneven edge to enhance a stimulation of said perineum region.

14. The apparatus of claim 12, wherein said at least one crest means further comprises at least one smooth edge.

15. The apparatus of claim 11, wherein said ridge means further comprises a plurality, each of said plurality capable of stimulating said perineum region.

16. The apparatus of claim 15 further comprising a depression between each of said plurality.

17. A method of stimulating a penile erection, the method comprising the steps of:
    placing a loop around a penis and scrotum;
    decreasing the diameter of said loop to help maintain said scrotum and/or penis on the outside of said loop;

positioning a rod having a point of stimulus downward between a user's legs and behind said scrotum; and adjusting the rod, to position said point of stimulus against a perineum region proximate to said scrotum and rectum, thereby forming an erection stimulator to stimulate said perineum region.

18. The method of claim 17 further comprising the step of applying muscular pressure to said rod from the thighs of the user.

19. The method of claim 17, wherein said point of stimulus further comprises at least one crest.

* * * * *